(12) United States Patent
Wu et al.

(10) Patent No.: US 6,656,506 B1
(45) Date of Patent: Dec. 2, 2003

(54) MICROPARTICLE COATED MEDICAL DEVICE

(75) Inventors: Steven Z. Wu, Santa Clara, CA (US); Syed F. A. Hossainy, Fremont, CA (US); Sameer Harish, Fremont, CA (US); Deborra Sanders-Millare, San Jose, CA (US); Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 4 days.

(21) Appl. No.: 09/851,877

(22) Filed: May 9, 2001

(51) Int. Cl.[7] .............................. A61K 9/14; A61K 9/16; A61K 9/50
(52) U.S. Cl. .................... 424/489; 424/490; 424/497
(58) Field of Search .................... 424/489, 490, 424/497

(56) References Cited

U.S. PATENT DOCUMENTS 5,665,382 A * 9/1997 Grinstaff et al.

* cited by examiner

Primary Examiner—Thurman K. Page
Assistant Examiner—Humera N. Sheikh

(57) ABSTRACT

A drug-loaded microparticle is applied to a medical device for subsequent application to biological tissues. A method of formulating a drug-loaded microparticle and applying it to the surface of a medical device, such as a stent, is disclosed. The drug-loaded microparticle is formulated by combining a drug with various chemical solutions. Specified sizes of the microparticles and amounts of drug(s) contained within the microparticles may be varied by altering the proportions of the chemicals/solutions. In addition to various drugs, therapeutic substances and radioactive isotopes may also be loaded into the microparticles. The drug-loaded microparticle are suspended in a polymer solution forming a polymer matrix. The polymer matrix may be applied to the entire surface or only selected portions of the medical device via dipping, spraying or combinations thereof.

9 Claims, 2 Drawing Sheets

MICROPARTICLE COATED MEDICAL DEVICE

BACKGROUND OF THE INVENTION

1. Field of the Invention

The present invention relates to a medical device for use in tissue and organ treatment and, in particular, to drug-loaded microparticles embedded within a matrix and applied to the medical device.

2. Related Art

A variety of surgical procedures and medical devices are currently used to relieve intraluminal constrictions caused by disease or tissue trauma. An example of one such procedure is percutaneous transluminal coronary angioplasty (PTCA). PTCA is a catheter-based technique whereby a balloon catheter is inserted into a blocked or narrowed coronary lumen of the patient. Once the balloon is positioned at the blocked lumen or target site, the balloon is inflated causing dilation of the lumen. The catheter is then removed from the target site thereby allowing blood to freely flow through the unrestricted lumen.

Although PTCA and related procedures aid in alleviating intraluminal constrictions, such constrictions or blockages reoccur in many cases. The cause of these recurring obstructions, termed restenosis, is due to the body's immune system responding to the trauma of the surgical procedure. As a result, the PTCA procedure may need to be repeated to repair the damaged lumen.

Stents or drug therapies, either alone or in combination with the PTCA procedure, are often used to avoid or mitigate the effects of restenosis at the surgical site. In general, stents are small, cylindrical devices whose structure serves to create or maintain an unobstructed opening within a lumen. The stents are typically made of stainless steel or a memory-responsive metal, such as Nitinol™ and are delivered to the target site via a balloon catheter. Although the stents are effective in opening the stenotic lumen, the foreign material and structure of the stents themselves may exacerbate the occurrence of restenosis or thrombosis.

Drugs or similar agents that limit or dissolve plaque and clots are used to reduce, or in some cases eliminate, the incidence of restenosis and thrombosis. Since the drugs are applied systemically to the patient, they are absorbed not only by the tissues at the target site, but by all areas of the body. As such, one drawback associated with the systemic application of drugs is that areas of the body not needing treatment are also affected. To provide more site-specific treatment, stents are frequently used as a means of delivering the drugs exclusively to the target site. By positioning the stent at the target site, the drugs can be applied directly to the area of the lumen requiring therapy or diagnosis.

In addition to the benefit of site-specific treatment, drug-loaded stents also offer long-term treatment and/or diagnostic capabilities. These stents include a biodegradable or absorbable polymer suspension that is saturated with a particular drug. In use, the stent is positioned at the target site and retained at that location either for a predefined period or permanently. The polymer suspension releases the drug into the surrounding tissue at a controlled rate based upon the chemical and/or biological composition of the polymer and drug.

The above-described devices and methods for treatment of restenosis and thrombosis, and other similar conditions not specifically described, offer many advantages to potential users. However, it has been discovered that such devices and methods may be deficient in their current drug-loading and drug-delivery characteristics. In particular, the amount or volume of drug capable of being delivered to the target site may be insufficient due to the limited surface area of the stent. In addition, drug release rates may also be inadequate since the rate at which the drug is released or delivered to the target site is a function of the chemical and/or biological properties of the polymer in which the drug is embedded.

SUMMARY

In view of the above, it is apparent that there is a need to provide a drug delivery device offering increased drug loading capabilities for medical devices and improved drug release rates. It is also desirable that the drug-delivery device allows one or more drugs to be released from the medical device to the target site. In addition, it is preferred that the device features enable one or more drugs to be released at variable and/or independent rates. There is also a need to provide a method of manufacturing such an improved drug delivery device that is convenient, efficient and cost effective.

In accordance with various aspects of the present invention, a small particle, such as a micro- and/or nano-particle (hereinafter referred to interchangeably as "microparticle"), is formed and loaded with a drug. The drug-loaded microparticle is formulated by combining a drug with various chemical solutions. In one embodiment, a microparticle can be formed by adding a drug-loaded solution containing a photoinitiator into a relatively inert bath. Light or similar energy is applied to the solution in the bath causing a photo-chemical reaction that produces one or more microparticles. In another embodiment, the drug-loaded solution is combined with a cross-linker solution and vigorously vortexed in a inert bath. The agitation together with the chemical reaction produces one or more microparticles. Specified sizes of the microparticles and amounts of drug(s) contained within the microparticles may be varied by altering the proportions of the above chemicals/solutions and by varying the process parameters during mixing. In addition to various drugs, therapeutic substances and radioactive isotopes may also be loaded into the microparticles.

Another aspect of the present invention is a method of applying a drug-loaded microparticle onto a medical device. A microparticle can be formed and loaded with one or more drugs, as described above. The drug-loaded microparticle is suspended in a polymer solution forming a polymer matrix. In one embodiment, the medical device is dipped in the polymer matrix so that a coating of the polymer matrix having a relatively smooth surface texture is applied over the entire surface of the medical device. In another embodiment, the entire surface of the medical device is spray coated with the polymer matrix. In yet another embodiment, only select portions of the medical device are coated with one or more polymer matrices.

Embodiments of the medical device make possible site specific treatment therapies. Coating different portions of an implantable medical device, with the disclosed microparticles loaded with various drugs advantageously allows site-specific treatment of discrete sections of the patient's lumen. In addition, by embedding the drug-loaded microparticle in a polymer, the resulting matrix can increase or decrease the release rate of the drug from the microparticle, depending on the type of polymer used. As such, drug release rates and thereby, for example, long term treatment or diagnostic capabilities, can be controlled. Moreover, the drugs can be suspended in a tissue-compatible polymer, such as silicone, polyurethane, polyvinyl alcohol, polyethylene, polyesters, swellable hydrogels, hyaluronate, various copolymers and blended mixtures thereof. Accordingly, a very selective cushioning effect can be attained.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION

Figure 1:
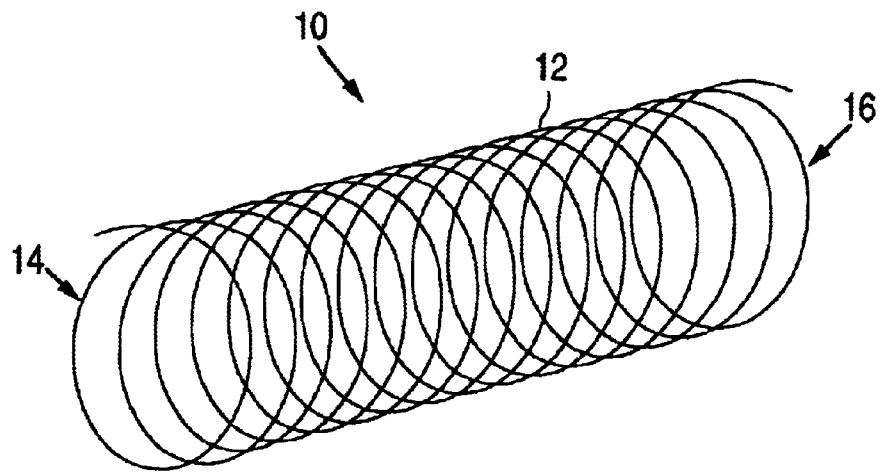
FIG. 1 is a side view of a drug-loaded medical device, e.g. stent, in accordance with an embodiment of the present invention.

The term "drug(s)," as used herein, refers to all therapeutic agents, diagnostic agents/reagents and other similar chemical/biological agents, including combinations thereof, used to treat and/or diagnose restenosis, thrombosis and related conditions. Examples of various drugs or agents commonly used include heparin, hirudin, antithrombogenic agents, steroids, ibuprofen, antimicrobials, antibiotics, tissue plasma activators, monoclonal antibodies, and antifibrosis agents.

A variety of drug classes and therapeutic substances may be used in accordance with the present disclosure. For example, therapeutic substances or agents may include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, actinomycin-D, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and anti-thrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, and dexamethasone.

While the above listed substances or agents are well known for preventative and therapeutic utility, the substances are listed by way of example and are not meant to be limiting. Other therapeutic substances which are currently available or that may be developed in the future are equally applicable. The treatment of patients using the above mentioned medicines is well-known to those of ordinary skill in the art.

FIG. 1 illustrates a drug-loaded medical device 10. Medical device can be any suitable medical device or prosthesis including, but not limited to, balloons, stents coverings, vascular grafts, and other implantable devices. For convenience and ease of comprehension, with no intent to limit the invention thereby, medical device 10 referenced in the text and figures of the present disclosure is an implantable stent.

As shown in FIG. 1, stent 10 includes one or more elongated elements 12 that are formed into a generally cylindrical or tubular shape having a first end 14 and a second end 16. The shape of the pre-formed elongated elements 12 may be straight, sinusoidal, V-shaped, or any other of a variety of patterns and shapes not disclosed herein. In addition, one or more interconnecting elements (not shown) may also be included to connect adjacent elongated elements 12 and increase the structural integrity of stent 10.

As with the elongated elements 12, the interconnecting elements may also have a variety of shapes and patterns including, but not limited to, circular, oval, straight, curved, and the like.

The elongated elements 12 and interconnecting elements of stent 10 are configured to allow stent 10 to easily expand and contract, thereby facilitating placement of stent 10 into an insertion device and, ultimately, a lumen of the body. To further enhance stent 10 flexibility, these components are typically fabricated from a metallic material or alloy, such as stainless steel, Nitinol™, tantalum, or other similar materials and/or combinations of such materials. The diameter of each elongated element 12 is typically within the range of approximately $3.9 \times 10^{-4}$ inch (0.001 cm) to $1.18 \times 10^{-3}$ inch (0.003 cm). Similarly, the diameter for each interconnecting element is approximately within the range of $3.9 \times 10^{-4}$ inch (0.001 cm) to $1.18 \times 10^{-3}$ inch (0.003 cm). Overall stent 10 diameter and length is approximately within the range of $0.1378 \pm 0.0394$ inch ($0.35 \pm 0.1$ cm) and $0.5118 \pm 0.1969$ inch ($1.3 \pm 0.5$ cm), respectively. The particular configuration of stent 10, such as choice of materials, size, structural characteristics, and the like, may vary based upon the location of the lesion, type of lesion and lumen dimensions of the target area.

Figure 2:
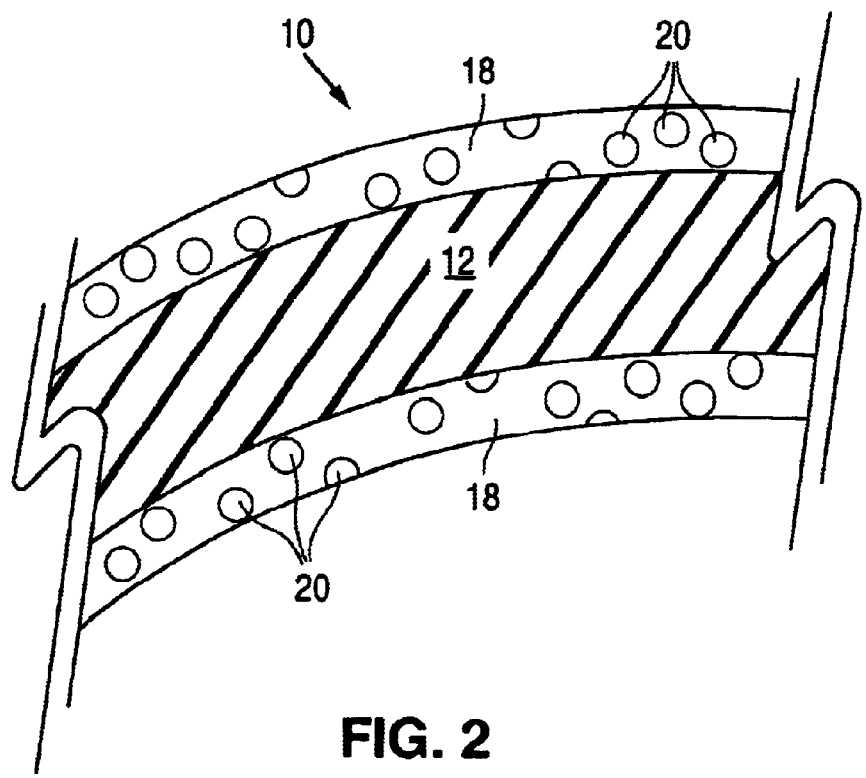
FIG. 2 is a cross-sectional view of a drug-coated elongated element in accordance with an embodiment of the present invention.

Referring to the embodiment of FIG. 2, to aid in the treatment and/or diagnosis of various conditions affecting the lumen, the entire surface of stent 10 can be coated with a polymer solution 18, which includes a suspension of drug-loaded microparticles 20, such as microspheres and/or nanospheres. It should be understood that the microparticles are not limited to spheres and thus may have any shape and remain within the scope of the invention.

Figure 3:
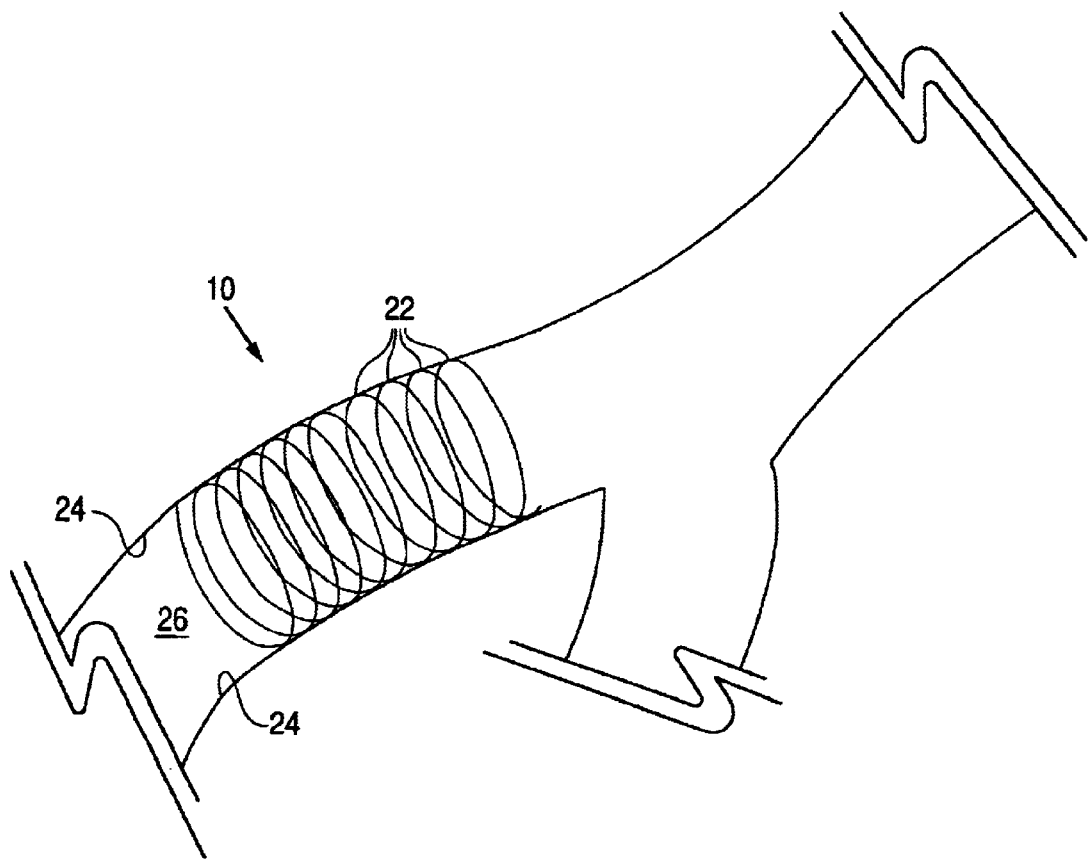
FIG. 3 illustrates a medical device inserted into the lumen of a patient in accordance with an embodiment of the present invention.

In this embodiment, the drug(s) remain suspended in the polymer matrix until stent 10 is deployed to the target site. When the surface 22 of stent 10 engages the wall 24 of the lumen 26, as shown in FIG. 3, the drug(s) disseminate from the polymer matrix (not shown) at a controlled release-rate. The drug(s) are absorbed into the tissue of the walls 24 of the lumen 26 that are in contact with stent 10.

FIG. 2 shows a detailed cross-sectional portion of an elongated element 12.

Various methods can be employed to formulate and drug-load the microparticles 20. The embodiments of the composition of drug-loaded microparticles 20 can be prepared by conventional methods where all components are combined then blended. In accordance with one embodiment, microparticles 20 can be prepared using a predetermined amount of a polymer or a prepolymer that is added to a predetermined amount of a solvent or a combination of solvents. The solvent is mutually compatible with the polymer and is capable of placing the polymer into solution at the concentration desired in the solution. Useful solvents can expand the chains of the polymer for maximum interaction with the surface of the medical device, such as a metallic surface of a stent. Examples of solvents can include, but are not limited to, dimethylsulfoxide (DMSO), Dimethyl Acetamide (DMAC), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

Microparticles 20 can be prepared in ambient pressure and under anhydrous atmosphere. If necessary, a free radical or UV initiator can be added to microparticles 20 for initiating the curing or cross-linking of the prepolymer. Heating and stirring and/or mixing can be employed to effect dissolution of the polymer into the solvent.

By way of example, and not limitation, the polymer can comprise from about 0.1% to about 35%, more narrowly about 2% to about 20% by weight of the total weight of the total solution, and the solvent can comprise from about 65% to about 99.9%, more narrowly about 80% to about 98% by weight, of the total weight of the total solution. A specific weight ratio is dependent on factors such as the material from which the implantable device is made and the geometrical structure of the device.

Sufficient amounts of an active ingredient are dispersed or dissolved in microparticles 20. The active ingredient should be in solution or suspension. If the active ingredient is not completely soluble in the composition, operations including mixing, stirring, and/or agitation can be employed to effect homogeneity. The active ingredient may be added so that the dispersion is in fine particles. The mixing of the active ingredient can be conducted in an anhydrous atmosphere, at ambient pressure, and at room temperature. In one embodiment, the active ingredient can minimize or inhibit the progression of neointimal hyperplasia. More specifically, the active ingredient is aimed at inhibiting abnormal or inappropriate migration and/or proliferation of smooth muscle cells and activation of inflammatory cells and platelets.

The following examples illustrate various drug-loading and microparticle formulation techniques, but do not limit possible techniques within the scope of the present invention. Note that "w/w" is an abbreviation for "by weight," used in chemistry and pharmacology to describe the concentration of a substance in a mixture or solution. For example, 25% w/w means that the mass of the substance is 25% of the total mass of the solution or mixture.

Example 1

A first solution is formulated using 25% w/w Polyethylene glycol diacrylate (PEGDA) dissolved in water. A water soluble drug, such as dexamethasone, is added at 5% w/w into the first solution, forming a second, PEGDA-Dexamethasone, solution. A third solution is formulated using 10% w/w 2,2, dimethoxy 2 phenyl acetophenone solution dissolved in vinyl pyrrolidone (VP) monomer. This third solution is the curing agent or photoinitiator solution. A final solution is formulated by adding 1 mL of the initiator solution per 9 mL of the PEGDA- Dexamethasone solution.

The process of fabricating a single microparticle 20 involves adding a drop of the final solution, using a 10 micro-liter pipette, into a viscous mineral oil or silicone oil bath. After adding the drop of solution to the bath, a 360 nm wavelength black ray UV lamp is used to cure the spherical droplet suspended in the bath. This results in a crosslinked, swollen PEGDA particle containing dexamethasone. The microparticle 20 is left to settle to the bottom of the vial containing the oil bath. The above process is repeated until the desired quantity of microparticles 20 is formed. The oil phase is then decanted off and the particles 20 are washed in a solvent, such as acetone, to remove the presence of any remaining oil.

Example 2

A first solution is formulated using 25% w/w PEGDA dissolved in deionized water. Actinomycin-D (Ac/D) is added at 5% w/w into the first solution, forming a second solution comprising a suspension of Ac/D in the PEGDA solution. A third (curing agent/photoinitiator) solution is formulated using 10% w/w 2,2, dimethoxy 2 phenyl acetophenone solution dissolved in VP monomer. A final solution is formulated by adding 1 mL of the initiator solution per 9 mL of the PEGDA-Ac/D suspension.

The process of fabricating a single microparticle 20 involves adding a drop of the final solution, using a 10 micro-liter pipette, into a viscous mineral oil or silicone oil bath. After adding the drop of solution to the bath, a 360 nm wavelength black ray UV lamp is used to cure the spherical droplet suspended in the bath. This results in a crosslinked, swollen PEGDA particle containing Ac/D. The microparticle 20 is left to settle to the bottom of the vial containing the oil bath. The above process is repeated until the desired quantity of microparticles 20 is formed. The oil phase is then decanted off and the particles 20 are washed in a solvent, such as acetone, to remove the presence of any remaining oil.

Example 3

A first solution is formulated using 25% w/w PEGDA dissolved in deionized water. Ac/D and dexamethasone are each added at 5% w/w into the first solution, forming a second solution comprising a suspension of Ac/D and a solution of dexamethasone in the PEGDA solution. A third (curing agent/photoinitiator) solution is formulated using 10% w/w 2,2, dimethoxy 2 phenyl acetophenone solution dissolved in VP monomer. A final solution is formulated by adding 1 mL of the initiator solution per 9 mL of the PEGDA-Ac/D suspension.

The final solution is added into a viscous mineral oil or silicone oil and vortexed vigorously. After the water-in-oil emulsion is formed, a 360 nm wavelength black ray UV lamp is used to cure the spherical droplets suspended in the bath. This results in crosslinked, swollen PEGDA particles containing Ac/D. The microparticles 20 are left to settle to the bottom of the vial containing the oil bath. The oil phase is then decanted off and the particles 20 are washed in a solvent, such as acetone, to remove the presence of any remaining oil.

Example 4

A first solution is formulated using 25% w/w VP dissolved in deionized water. PEGDA, having a molecular weight of 1000, is added at 8% w/w into the first solution, together with 5% w/w dexamethasone, forming a second solution comprising a suspension of PEGDA-dexamethasone in the VP solution. A third (curing agent/photoinitiator) solution is formulated using 10% w/w 2,2, dimethoxy 2 phenyl acetophenone solution dissolved in VP monomer. A final solution is formulated by adding 1 mL of the initiator solution per 9 mL of the VP-Dexamethasone suspension.

The process of fabricating a single microparticle 20 involves adding a drop of the final solution, using a 10 micro-liter pipette, into a viscous mineral oil or silicone oil bath. After adding the drop of solution to the bath, a 360 nm wavelength black ray UV lamp is used to cure the spherical droplet suspended in the bath. This results in a crosslinked, swollen VP particle containing Dexamethasone. The microparticle 20 is left to settle to the bottom of the vial containing the oil bath. The above process is repeated until the desired quantity of microparticles 20 is formed. The oil phase is then decanted off and the particles 20 are washed in a solvent, such as acetone, to remove the presence of any remaining oil.

Example 5

A first solution is formulated using 15% w/w VP dissolved in deionized water. PEGDA, having a molecular weight of 1000, is added at 15% w/w into the first solution. In addition, Ac/D is also added at 5% w/w, forming a second solution comprising a suspension of PEGDA and Ac/D in the VP solution. A third (curing agent/photoinitiator) solution is formulated using 10% w/w 2,2, dimethoxy 2 phenyl acetophenone solution dissolved in VP monomer. A final solution is formulated by adding 1 mL of the initiator solution per 9 mL of the PEGDA/Ac/D-VP suspension.

The final solution is added into a viscous mineral oil or silicone oil and vortexed vigorously. After the water-in-oil emulsion is formed, a 360 nm wavelength black ray UV lamp is used to cure the spherical droplets suspended in the bath. This results in crosslinked, swollen PEGDA particles containing Ac/D. The microparticles 20 are left to settle to the bottom of the vial containing the oil bath. The oil phase is then decanted off and the particles 20 are washed in a solvent, such as acetone, to remove the presence of any remaining oil.

Example 6

A first solution is formulated using 10% w/w Poly Alginate (PAIg) dissolved in deionized water. Ac/D is added at 5% w/w into the first solution, forming a second solution comprising a suspension of Ac/D in the PAIg solution. A third solution is formulated using 10% w/w Calcium chloride solution dissolved in deionized water. This third solution is the curing agent or cross-linker solution.

The Ac/D-PAIg suspension is added into the cross-linker solution and vortexed vigorously. After the divalention cross-linked Alginate particles are formed, the particles 20 are left to settle to the bottom of the vial containing the cross-linker solution. The cross-linker phase is decanted off and the particles 20 are then washed in deionized water.

Example 7

A first solution is formed by dissolving 10% w/v cellulose acetate phthalate (CAP), available from Schutz & Co., Germany, in a solvent, such as acetone. Note that "w/v" is an abbreviation for "weight by volume, "a phrase used in chemistry and pharmacology to describe the concentration of a substance in a mixture or solution. The weight by volume is the mass (in grams) of the substance dissolved in or mixed with 100 milliliters of solution or mixture. For example, the concentration of CAP in a solvent, such as acetone, is 0.10% w/v, meaning that there is 0.10 gram of CAP per 100 milliliters of acetone. Thus 1% w/v is equal to 1 gram per deciliter (g/dL) or 10 grams per liter.

A second solution is formed by combining 100 mL of liquid paraffin (or other similar mixture of hydrocarbons) with 1% w/v Span 80 in a 400 mL beaker. This solution is then agitated at 400 rpm using a 3-bladed stirrer (having a 5 cm diameter) connected to a stirring motor (e.g., Tecmatic SD2).

One gram of Ac/D is dissolved in 20 mL of the first solution. This solution is then poured into the second solution, forming a final solution. Evaporation of the solvent from the final solution proceeds for 24 hours at 30° C., producing residual microparticles 20 at the bottom of the beaker. The microparticles 20 are collected in a Buchner, or equivalent, filter and washed in 50 mL of ether. The microparticles 20 are then allowed to dry at room temperature for 24 hours.

Example 8

A first solution is formed by dissolving 10% w/v cellulose acetate phthalate (CAP), available from Schutz & Co., Germany, in a solvent, such as acetone. A second solution is formed by combining 100 mL of liquid paraffin with 1% w/v Span 80 in a 400 mL beaker. This solution is then agitated at 400 rpm using a 3-bladed stirrer (having a 5 cm diameter) connected to a stirring motor (e.g., Tecmatic SD2).

One gram of Trapidil is dissolved in 20 mL of the first solution. This mixture is then poured into the second solution. Evaporation of the solvent from the mixture/solution proceeds for 24 hours at 30° C., producing residual microparticles 20 at the bottom of the beaker. The microparticles 20 are collected in a Buchner, or equivalent, filter and washed in 50 mL of ether. The microparticles 20 are then allowed to dry at room temperature for 24 hours.

The above-described formulation examples are specific to drug-loaded microparticles 20. Other materials, such as PEG-gels, PLA (polylactic acid), PCL (poly caprolactone), and the like, may also be used to formulate drug-loadable microparticles 20 using similar methods to those described above. Further, by modifying the pipette/dropper size or vortex speed, microparticles 20 of varying sizes may be formed. Smaller or larger sized microparticles 20 may be preferred to more accurately control drug volumes and duration of release rates.

In some embodiments, a second drug can be applied in the matrix polymer, such as EVAL. PEGDA hydrogel nanoparticles can be combined with other drug loaded nanoparticles to obtain additional effects, such as a cushioning effect.

In addition to drugs, radioactive isotopes may also be loaded into the microparticles 20, utilizing relatively similar formulation techniques. Examples of radioactive isotopes include, but are not limited to, $^{32}$P, $^{55,56,57}$Co, $^{52}$Mg, and $^{55}$Fe. In one embodiment, nano-sized gold-particles containing one or multiple radioisotopes are used to create a radiopaque/radiotherapy stent that is easily tracked through or located within the body of the patient.

To increase overall drug-loading on stent 10, the drug-loaded microparticles 20, shown in FIG. 2, are coated onto the entire surface of stent 10 with a biocompatible polymer solution 18. Any suitable polymer solutions 18 can be used, such as low-density polyethylene, poly (ethylene glycol) and other similar solutions, such as polycaprolactone, ethylene vinyl acetate, polyvinyl alcohol and the like. In one embodiment, the polymer solution 18 can be ethylene vinyl alcohol, which is functionally a very suitable choice of polymer. Ethylene vinyl alcohol copolymer, commonly known by the generic name EVOH or by the trade name EVOH, refers to copolymers including residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 47%. Typically, 44 mole percent ethylene is suitable. Ethylene vinyl alcohol copolymers are available commercially from companies such as Aldrich Chemical Company, Milwaukee, Wis., or EVOH Company of America, Lisle, Ill., or can be prepared by conventional polymerization procedures that are well known to one of ordinary skill in the art. The copolymer possesses good adhesive qualities to the surface of stent 10, particularly stainless steel surfaces, and has illustrated the ability to expand with stent 10 without any significant detachment of the copolymer from the surface of stent 10.

If polymer solution 18 is used with a solvent, the solvent should be mutually compatible with polymer solution 18 and should be capable of placing polymer solution 18 into solution at the concentration desired in the solution. Useful solvents should also be able to expand the chains of the polymer for maximum interaction with the surface of the device, such as the metallic surface of stent 10. Examples of solvent can include, but are not limited to, dimethylsulfoxide (DMSO), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

A suitable fluid having a high capillary permeation can be added to polymer solution 18 to enhance the wetting for a more uniform coating application. The wetting fluid, typically, should have a viscosity not greater than about 50 centipoise, narrowly about 0.3 to about 5 centipoise, more narrowly about 0.4 to about 2.5 centipoise. The wetting fluid should be mutually compatible with polymer solution 18 and the solvent and should not precipitate polymer solution 18. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof.

In accordance with another embodiment, a fluid can be added to the composition to enhance the wetting of the composition for a more uniform coating application. To enhance the wetting of the composition, a suitable fluid typically has a high capillary permeation. Capillary permeation or wetting is the movement of a fluid on a solid substrate driven by interfacial energetics. The wetting fluid should be mutually compatible with the polymer and the solvent and should not precipitate the polymer. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof.

By way of example and not limitation, the polymer can comprise from about 0.1% to about 35%, more narrowly from about 2% to about 20% by weight of the total weight of the composition; the solvent can comprise from about 19.9% to about 98.9%, more narrowly from about 58% to about 84% by weight of the total weight of the composition; the wetting fluid can comprise from about 1% to about 80%, more narrowly from about 5%, to about 40% by weight of the total weight of the composition. The specific weight ratio of the wetting fluid depends on the type of wetting fluid employed and type of and the weight ratio of the polymer and the solvent. More particularly, tetrahydrofuran used as the wetting fluid can comprise, for example, from about 1% to about 44%, more narrowly about 21% by weight of the total weight of the solution. Dimethylformamide used as the wetting fluid can comprise, for example, from about 1% to about 80%, more narrowly about 8% by weight of the total weight of the solution 1-butanol used as the wetting fluid can comprise, for example, from about 1% to about 33%, more narrowly about 9% by weight of the total weight of the solution. N-butyl acetate used as the wetting fluid can comprise, for example, from about 1% to about 34%, more narrowly about 14% by weight of the total weight of the solution. Dimethyl acetamide used as the wetting fluid can comprise, for example, from about 1% to about 40%, more narrowly about 20% by weight of the total weight of the solution.

In accordance with one embodiment, the microparticles 20 are embedded within the polymer solution 18, thereby forming a polymer matrix that securely adheres to the surface of stent 10. In addition, depending on the polymer solution 18 and the porosity of the micro/nano-spheres 20, the drug release rates may also be controlled. With the use of a polymer solution 18, such as ethylene vinyl alcohol copolymer, polycaprolactone, poly(lactide-co-glycolide), poly(hydroxybutyrate), and the like, the deposited polymer solution 18 should be exposed to a heat treatment at temperature range greater than about the glass transition temperature (Tg) and less than about the melting temperature (Tm) of the polymer. Stent 10 should be exposed to the heat treatment for any suitable duration of time, which would allow for the formation of the coating on the surface of stent 10 and allows for the evaporation of the solvent or combination of solvent and wetting fluid, if necessary. It is understood that essentially all of the solvent and the wetting fluid will be removed from the composition but traces or residues can remain blended with the polymer. The Tg and Tm for the polymers used in the embodiments of the present invention are attainable by one or ordinary skill in the art.

Table 1 lists the $T_g$ and $T_m$ for some exemplary polymers which can be used in embodiments of the present invention. $T_g$ and $T_m$ of polymers are attainable by one or ordinary skill in the art. The cited exemplary temperature and time for exposure is provided by way of illustration and it is not meant to be limiting.

TABLE 1

| Polymer | $T_g$ (° C.) | $T_m$ (° C.) | Exemplary Temperature (° C.) | Exemplary Duration of Time For Heating |
|---|---|---|---|---|
| EVOH | 55 | 165 | 140 | 4 hours |
| polycaprolactone | −60 | 60 | 50 | 2 hours |
| ethylene vinyl acetate (e.g., 33% vinylacetate content) | 36 | 63 | 45 | 2 hours |
| Polyvinyl alcohol | 75–85* | 200–220* | 165 | 2 hours |

*Exact temperature depends on the degree of hydrolysis which is also known as the amount of residual acetate.

With the use of one of the aforementioned thermoplastic polymers, the use of initiators may be required. By way of example, epoxy systems consisting of diglycidyl ether of bisphenol A resins can be cured with amine curatives, thermoset polyurethane prepolymers can cured with polyols, polyamines, or water (moisture), and acrylated urethane can be cured with UV light. Further discussion of polymers, solvents, wetting fluids and initiators are disclosed in commonly assigned U.S. application Ser. No. 09/750,595, entitled "Coating for Implantable Devices and a Method of Forming the Same", filed Dec. 28, 2000, which is herein incorporated by reference for all purposes.

The following methods may be used to embed the micro/nano-spheres 20 in the polymer solution 18 and apply the resulting matrix to the surface of stent 10. Although several methods are disclosed, it is to be understood that the following list is not inclusive. Other similar methods may also be used and are within the scope of the presently claimed invention.

Method 1

EVOH Solution Formulation: An EVOH solution is made by adding 10 grams of EVOH into 90 grams of DMAC. The components are dissolved to form a solution by heating the mixture to 50° C., with constant stirring.

Stent Coating Process: PEGDA microparticles 20, ranging in size from approximately 0.5 to 2.0 microns (0.1×10 mm to 0.5×10 mm) in length, are suspended in the EVOH solution by adding 20 grams of microparticles 20 into 80 grams of the EVOH solution. The final suspension is constantly agitated or stirred to prevent flocculation. Stents 10 are dipped in the final suspension and then centrifuged at 6,000 rpm for 60 seconds resulting in a coating having a relatively smooth surface texture.

Method 2

EVOH Solution Formulation: see Method 1 (above).

Stent Coating Process: see Method 1 (above). In addition, a co-solvent solution is formulated by combining 2% EVOH in 1:1 w/w DMSO:DMF. Stents 10 are then spray-coated with a top coat of a co-solvent solution so that the initial microparticle 20 coating is completely covered by the EVOH top coat. This top coat provides a means to control drug release rates and obtain smooth surface textures.

Method 3

EVOH Solution Formulation: see Method 1 (above).

Stent Coating Process: Ac/D loaded CAP microparticles 20, ranging in size from approximately 0.5 to 2.0 microns (0.1×10$^{-4}$ mm to 0.5×10$^{-4}$ mm) in length, are suspended in the EVOH solution by adding 20 grams of microparticles to 80 grams of EVOH solution. To prevent flocculation, the final solution is constantly stirred. Stents 10 are then dipped in the final suspension and then centrifuged at 6,000 rpm for 60 seconds, resulting in a coating having a relatively smooth surface texture. The coated stents 10 are then spray-coated with a top coat of a co-solvent solution containing 2% EVOH in DMAC. This top coat provides a means to control drug release rates and obtain smooth surface textures.

Method 4

EVOH Solution Formulation: see Method 2 (above). Prior to applying the polymer matrix, described below, stents 10 are initially coated with a layer of EVOH by dipping, spraying or similar coating techniques.

Stent Coating Process: PEGDA microparticles 20, ranging in size from approximately 0.5 to 2.0 microns (0.1×10$^{-4}$ mm to 0.5×10$^{-4}$ mm) in length, are suspended in methanol by adding 50 grams of microparticles 20 into 50 grams of methanol. The final suspension (i.e. polymer matrix) is constantly stirred to prevent flocculation. Stents 10 are dipped in the final suspension and then centrifuged at 2,000 rpm for 60 seconds resulting in a coating having a relatively smooth surface texture. The coated stents 10 are then spray-coated with a co-solvent solution containing 2% EVOH in 1:1 w/w DMSO:DMF.

Method 5

EVOH Solution Formulation: see Method 4 (above).

Stent Coating Process: PEGDA microparticles 20, ranging in size from approximately 0.5 to 2.0 microns (0.1×10$^{-4}$ mm to 0.5×10$^{-4}$ mm) in length, are suspended in methanol by adding 50 grams of microparticles 20 into 50 grams of methanol. The final suspension is constantly stirred to prevent flocculation. Stents 10 are selectively dipped, e.g. only the ends 14, 16 of each stent 10 are dipped, in the final suspension and then centrifuged at 1,000 rpm for 30 seconds resulting in a coating having a relatively smooth surface texture. The coated stents 10 are then spray-coated with a top coat of a co-solvent solution containing 2% EVOH in 1:1 w/w DMSO:DMF. The initial selective dipping of stent 10, together with the sprayed top-coat, produces a hydrogel cushion at each end 14, 16 of stent 10. This hydrogel cushion reduces or eliminates trauma to the lumen or vessel due to contact with un-coated ends 14, 16 of stent 10.

Method 6

EVOH Solution Formulation: see Method 4 (above).

Stent Coating Process: VP microparticles 20, ranging in size from approximately 0.5 to 2.0 microns (0.1×10$^{-4}$ mm to 0.5×10$^{-4}$ mm) in length, are suspended in methanol by adding 50 grams of microparticles 20 into 50 grams of methanol. The final suspension is constantly stirred to prevent flocculation. Stents 10 are dipped in the final suspension and then centrifuged at 2,000 rpm for 60 seconds resulting in a coating having a relatively smooth surface texture. The coated stents 10 are then spray-coated with a co-solvent solution containing 2% EVOH in 1:1 w/w DMSO:DMF, thereby completely covering the microparticle 20 coating with a top-coat of EVOH.

Alternative methods of applying drug-loaded microparticles 20 onto the surface of a stent 10, including various combinations of methods, are also within the scope of the present disclosure. The type of microparticle 20, drug and layering technique provide increased volume of drug-loading on stent 10 and controllable drug release rates. For example, in one embodiment, the entire stent 10 is coated with a first layer of EVOH as described above. A first suspension of Ac/D loaded CAP microparticles 20 and a second suspension of PEGDA microparticles 20 (formulated according to the methods described above) are selectively applied as a second layer on stent 10. In particular, the first end of stent 10 is coated with a layer of the first suspension and the second end 16 of stent 10 is coated with a layer of the second suspension. This embodiment allows stent 10 to selectively deliver two types of drugs to two different target sites in the lumen.

In an alternate embodiment, the entire stent 10 is coated with a first layer of EVOH. A suspension made of a combination of Ac/D loaded CAP microparticles 20 and PEGDA microparticles 20 is formulated and applied as a second layer on stent 10. The ratio of Ac/D loaded CAP microparticles 20 to PEGDA microparticles 20 in the suspension is variable based upon the desired treatment or diagnosis. In addition, the second layer of the suspension may either be applied over the entire stent 10 or over only selective portions of stent 10, using dipping, spraying, or other similar methods.

In yet another embodiment, the entire stent 10 is coated with a first layer of EVOH. A second layer comprising a suspension formulated from a combination of Ac/D loaded CAP microparticles 20, PEGDA microparticles 20 and VP microparticles 20 is selectively applied to stent 10. Alternatively, only selected portions of stent 10 may be coated with a variety of second layers. For example, a first portion of stent 10 may be coated with a suspension consisting of Ac/D loaded CAP microparticles 20 and VP microparticles 20, a second portion with only PEGDA microparticles 20, and a third portion with PEGDA microparticles 20 and VP microparticles 20.

In yet another embodiment, microparticles 20 can be layered by depositing a first layer followed by a top-coating. The top-coating can be, for example, a blank matrix polymer. A second layering of microparticle 20 can then be applied over the top-coating. In one embodiment, the second layering of microparticles 20 can be the same type of microparticles as the first layering or, alternatively, the second layering can include a different type of microparticles 20 (i.e., a different formulation) from the first layering of microparticles 20. The process of layering microparticles intermittent with the top-coating can be repeated to provide layering patterns according to the requirements of the desired treatment or diagnosis.

Embodiments of the device make possible site specific treatment therapies. Coating different portions of a stent, or other implantable medical device, with the disclosed microparticles loaded with various drugs advantageously allows site-specific treatment of discrete sections of the patient's lumen. In addition, by embedding the drug-loaded microparticle in a polymer, the resulting matrix can increase or decrease the release rate of the drug from the microparticle, depending on the type of polymer used. As such, drug release rates and, for example, long term treatment or diagnostic capabilities, can be controlled.

The scope of the present invention also includes alternative stent embodiments having various combinations of drugs and layering patterns/methods. The particular drug(s) and layering patterns on the stent are configured according to the requirements of the desired treatment or diagnosis.

Although the invention has been described in terms of particular embodiments and applications, one of ordinary sill in the art, in light of this teaching, can generate additional embodiments and modifications without departing from the spirit of or exceeding the scope of the claimed invention. Accordingly, it is to be understood that the drawings and descriptions herein are proffered by was of example to facilitate comprehension of the invention and should not be construed to limit the scope thereof.

What is claimed is:

1. A drug-loaded microparticle formulation method comprising:
   adding a volume of a chemical to water to form a first solution;
   adding a volume of a water soluble drug to said first solution to form a second solution;
   combining a volume of a curing agent solution with a volume of said second solution to form a final solution;
   adding a volume of said final solution to an oil bath;
   forming one or more droplets of said chemical containing said drug by curing said chemical;
   removing the droplets form said oil bath;
   rinsing said droplets to remove said oil;
   adding said droplets to a stent coating composition, said stent coating composition being in a fluid state such that said droplets are suspended in said stent coating composition, said stent coating composition comprising an ethylene vinyl alcohol copolymer; and
   causing said stent coating composition to solidify into a film layer wherein said droplets of said chemical containing said drug are embedded within said ethylene vinyl alcohol copolymer.

2. The method of claim 1, wherein said chemical comprises a chemical taken from the group consisting of polyethylene glycol diacrylate (PEGDA), vinyl pyrrolidone, and poly alginate.

3. The method of claim 1, wherein said oil bath comprises a vortexed oil bath.

4. The method of claim 1, wherein said water soluble drug comprises a water soluble drug taken from the group consisting of dexamethasone and actinomycine-D.

5. The method of claim 1, wherein said curing agent solution comprises 2,2, dimethoxy 2 phenyl acetophenone solution dissolved in vinyl pyrrolidone.

6. A drug-loading micro-particle formulation method, comprising:
   formulating a mixture of a polymeric material and a drug in a volume of water;
   adding the formulation to an oil based solution;
   forming particles of the polymeric material containing the drug;
   extracting the particles from the oil based solution;
   combining the particles to a fluid form of a stent coating material; and
   solidifying the stent coating material into a thin film wherein the thin film contains the particles.

7. The method of claim 6, wherein the particles are formed by curing the polymeric material.

8. The method of claim 6, wherein the polymeric material is a polyethylene glycol based substance and the stent coating material includes ethylene vinyl alcohol copolymer.

9. The method of claim 6, wherein the formulation is used as a coating for a stent for the delivery of the drug, and wherein the drug is used for the treatment of restenosis.

* * * * *